(12) United States Patent
Vartanian et al.

(10) Patent No.: US 9,764,160 B2
(45) Date of Patent: Sep. 19, 2017

(54) REDUCING ABSORPTION OF RADIATION BY HEALTHY CELLS FROM AN EXTERNAL RADIATION SOURCE

(75) Inventors: Harry Vartanian, Philadelphia, PA (US); Jaron Jurikson-Rhodes, Philadelphia, PA (US)

(73) Assignee: HJ Laboratories, LLC, Bryn Mawr, PA (US)

( * ) Notice: Subject to any disclaimer, the term of this patent is extended or adjusted under 35 U.S.C. 154(b) by 888 days.

(21) Appl. No.: 13/337,595

(22) Filed: Dec. 27, 2011

(65) Prior Publication Data

US 2012/0091371 A1    Apr. 19, 2012

(51) Int. Cl.
*A61N 5/10*    (2006.01)

(52) U.S. Cl.
CPC .... *A61N 5/1042* (2013.01); *A61N 2005/1094* (2013.01)

(58) Field of Classification Search
CPC  G21K 1/00; G21K 1/08; G21K 1/087; G21K 1/14; G21K 1/16; A61N 1/36071; A61N 1/36082; A61N 1/3787; A61N 2005/1094; H01J 35/16
USPC .......... 607/61, 66, 72, 75, 76, 116–118, 148
See application file for complete search history.

(56) References Cited

U.S. PATENT DOCUMENTS

| | | | |
|---|---|---|---|
| 3,789,832 A | 2/1974 | Damadian | |
| 5,051,592 A | 9/1991 | Trotel | |
| 5,866,912 A | 2/1999 | Slater et al. | |
| 6,093,456 A | 7/2000 | England et al. | |
| 6,124,834 A | 9/2000 | Leung et al. | |
| 6,225,622 B1 | 5/2001 | Navarro | |
| 6,322,560 B1 | 11/2001 | Garbagnati et al. | |
| 6,639,234 B1 | 10/2003 | Badura et al. | |
| 6,693,283 B2 | 2/2004 | Eickhoff et al. | |
| 6,703,632 B1 | 3/2004 | Macklis et al. | |
| 6,814,694 B1 | 11/2004 | Pedroni | |
| 6,828,786 B2 | 12/2004 | Scherer et al. | |
| 6,873,123 B2 | 3/2005 | Marchand et al. | |
| 6,936,046 B2 | 8/2005 | Hissong et al. | |
| 6,957,108 B2 | 10/2005 | Turner et al. | |
| 7,138,771 B2 | 11/2006 | Bechthold et al. | |
| 7,160,239 B2 | 1/2007 | Ichikawa et al. | |
| 7,317,190 B2 | 1/2008 | Ertel et al. | |
| 7,348,579 B2 | 3/2008 | Pedroni | |
| 7,375,357 B2 | 5/2008 | Kaufman | |
| 7,382,857 B2 | 6/2008 | Engel | |

(Continued)

FOREIGN PATENT DOCUMENTS

| | | |
|---|---|---|
| CN | 102160790 A | 8/2011 |
| WO | 9608999 A1 | 3/1996 |
| WO | 2006/119379 A1 | 11/2006 |

OTHER PUBLICATIONS

"Antenna Patterns", downloaded before Dec. 27, 2011.

(Continued)

*Primary Examiner* — Charles A Marmor, II
*Assistant Examiner* — Carrie R Dorna
(74) *Attorney, Agent, or Firm* — Volpe and Koenig, P.C.

(57) ABSTRACT

A semi-flexible rod may have a rounded tip having exposed metal conductor elements that produce an adaptive electrical field or an adaptive magnetic field. The adaptive electrical field or the adaptive magnetic field may be adjusted in order to capture a stray x-ray photon near an in-vivo target area of cancer cells.

1 Claim, 7 Drawing Sheets

(56) References Cited

U.S. PATENT DOCUMENTS

| | | | |
|---|---|---|---|
| 7,419,500 B2 | 9/2008 | Marko et al. | |
| 7,500,952 B1 | 3/2009 | Chiang et al. | |
| 7,559,945 B2 | 7/2009 | Breden et al. | |
| 7,570,063 B2 | 8/2009 | Van Veen et al. | |
| 7,643,965 B2 | 1/2010 | Zhang | |
| 7,755,068 B2 | 7/2010 | Ma et al. | |
| 7,787,937 B2 | 8/2010 | Scarantino et al. | |
| 7,791,051 B2 | 9/2010 | Beloussov et al. | |
| 7,791,290 B2 | 9/2010 | Gorrell et al. | |
| 7,792,566 B2 | 9/2010 | Roland et al. | |
| 7,801,988 B2 | 9/2010 | Baumann et al. | |
| 7,826,854 B2 | 11/2010 | Hovers et al. | |
| 7,828,733 B2 | 11/2010 | Zhang et al. | |
| 7,835,492 B1 | 11/2010 | Sahadevan | |
| 7,868,482 B2 | 1/2011 | Greene et al. | |
| 7,902,530 B1 | 3/2011 | Sahadevan | |
| 7,962,197 B2 | 6/2011 | Rioux et al. | |
| 8,024,048 B2 | 9/2011 | Schroeppel et al. | |
| 8,027,712 B2 | 9/2011 | Sioshansi et al. | |
| 8,030,627 B2 | 10/2011 | Gentry et al. | |
| 8,067,748 B2 | 11/2011 | Balakin | |
| 8,111,806 B2 | 2/2012 | Amelia et al. | |
| 8,111,886 B2 | 2/2012 | Rousso et al. | |
| 8,121,669 B2 | 2/2012 | Porikli et al. | |
| 8,129,699 B2 | 3/2012 | Balakin | |
| 8,129,701 B2 | 3/2012 | Al-Sadah et al. | |
| 8,130,906 B2 | 3/2012 | Sendai | |
| 8,174,931 B2 | 5/2012 | Vartanian et al. | |
| 8,661,573 B2 | 3/2014 | Shafer et al. | |
| 2006/0202891 A1 | 9/2006 | Izumi et al. | |
| 2006/0235484 A1* | 10/2006 | Jaax et al. | 607/46 |
| 2006/0280689 A1 | 12/2006 | Xiang et al. | |
| 2007/0031337 A1 | 2/2007 | Schulte | |
| 2007/0184020 A1 | 8/2007 | Kalbe et al. | |
| 2008/0082026 A1 | 4/2008 | Schmidt et al. | |
| 2008/0125647 A1 | 5/2008 | Rosengren et al. | |
| 2008/0188772 A1 | 8/2008 | Broennimann et al. | |
| 2009/0054737 A1 | 2/2009 | Magar et al. | |
| 2009/0063110 A1 | 3/2009 | Failla et al. | |
| 2009/0088618 A1 | 4/2009 | Arneson et al. | |
| 2009/0102612 A1 | 4/2009 | Dalbow et al. | |
| 2009/0132015 A1 | 5/2009 | Miller et al. | |
| 2009/0182426 A1* | 7/2009 | Von Arx | A61B 5/0031 623/11.11 |
| 2009/0198309 A1 | 8/2009 | Gowda et al. | |
| 2009/0201206 A1 | 8/2009 | Li et al. | |
| 2009/0289181 A1 | 11/2009 | Wickman | |
| 2009/0294300 A1 | 12/2009 | Kanzius et al. | |
| 2009/0306654 A1 | 12/2009 | Garbagnati | |
| 2010/0016932 A1 | 1/2010 | Weinberg | |
| 2010/0019918 A1 | 1/2010 | Avital et al. | |
| 2010/0051833 A1 | 3/2010 | Guertin et al. | |
| 2010/0074400 A1 | 3/2010 | Sendai | |
| 2010/0125225 A1 | 5/2010 | Gelbart et al. | |
| 2010/0140500 A1 | 6/2010 | Jesseph et al. | |
| 2010/0179522 A1 | 7/2010 | Companion et al. | |
| 2010/0187446 A1 | 7/2010 | Dilmanian et al. | |
| 2010/0202587 A1 | 8/2010 | Schmidt et al. | |
| 2010/0260317 A1 | 10/2010 | Chang et al. | |
| 2010/0272241 A1 | 10/2010 | Amelia et al. | |
| 2010/0298821 A1 | 11/2010 | Garbagnati | |
| 2010/0301782 A1 | 12/2010 | Yamamoto et al. | |
| 2011/0085640 A1 | 4/2011 | Fadler | |
| 2011/0125143 A1 | 5/2011 | Gross et al. | |
| 2011/0127443 A1 | 6/2011 | Comer et al. | |
| 2011/0130709 A1 | 6/2011 | N'diaye | |
| 2011/0166437 A1 | 7/2011 | Chang et al. | |
| 2011/0224477 A1 | 9/2011 | Issels | |
| 2011/0240874 A1 | 10/2011 | Iwata | |
| 2011/0270184 A1 | 11/2011 | Gunday et al. | |
| 2011/0284757 A1 | 11/2011 | Butuceanu et al. | |
| 2011/0306881 A1 | 12/2011 | Liu et al. | |
| 2012/0022409 A1 | 1/2012 | Gertner et al. | |

OTHER PUBLICATIONS

Vlachos et al., "Automatic Deactivation in Phased Array Probe for Human Prostate Magnetic Resonance Imaging at 1.5T", World Academy of Science, Engineering and Technology 30, Jul. 31, 2007, pp. 270-275.

Hawk, Ray, "What is a nanoantenna", Dec. 7, 2011, www.wisegeek.com/what-is-a-nanoantenna.htm.

Csaki et al., "A Parallel Approach for Subwavelength Molecular Surgery using Gene-specific Positioned Metal Nanoparticles as Laser Light Antennas", Jan. 24, 2007, PubMed.

Palta, Jatinder R., "Perils of Proton Therapy", downloaded before Dec. 27, 2007, Gainesville, Florida.

Aminov et al., "Beam Phase Detection for Proton Therapy Accelerators", Proceedings of 2005 Particle Accelerator Conference, May 16-20, 2005, pp. 1-3, IEEE, Knoxville, Tennessee.

Mumot et al., "Proton Range Verification using a Range Probe: Definition of Concept and Initial Analysis", Physics in Medicine and Biology, vol. 55, No. 16, Aug. 3, 2010.

Adey, W. R., "Cell Membranes: The Electromagnetic Environment and Cancer Promotion", Neurochemical Research, 1988, pp. 671-677, vol. 13, No. 7, Plenum Publishing Corporation.

Petit, M., Bort, G., Doan, B.-T., Sicard, C., Ogden, D., Scherman, D., Ferroud, C. and Dalko, P. I., "X-ray Photolysis To Release Ligands from Caged Reagents by an Intramolecular Antenna Sensitive to Magnetic Resonance Imaging." , Oct. 4, 2011, Angew. Chem. Int. Ed., 50: 9708-9711. Epub: Jul. 21, 2011. http://www.chemistryviews.org/details/ezine/1308465/Unmasked_by_X-rays.html.

Beaty, B., "'Energy-sucking' Radio Antennas, N. Tesla's Power Receiver," updated Sep. 1999, http://amasci.com/tesla/tesceive.html.

von Maltzahn, G., Park, J.H., Agrawal, A., Bandaru, N.K., Das, S.K., Sailor, M.J., Bhatia, S.N., "Computationally Guided Photothermal Tumor Therapy Using Long-Circulating Gold Nanorod Antennas," Cancer Res. May 1, 2009, 69 (9) :3892-3900. Epub: Apr. 14, 2009. http://www.ncbi.nlm.nih.gov/pmc/articles/PMC2712876/.

"Radiation," Wikipedia, http://en.wikipedia.org/wiki/Radiation. Downloaded on Jun. 13, 2014.

"Nantenna," Wikipedia, http://en.wikipedia.org/wiki/Nantenna. Downloaded on Jun. 13, 2014.

\* cited by examiner

REDUCING ABSORPTION OF RADIATION BY HEALTHY CELLS FROM AN EXTERNAL RADIATION SOURCE

FIELD OF INVENTION

This application is related to an apparatus and method for reducing absorption of radiation by healthy cells from an external radiation source provided to a living organism by using a smart or adaptive medical device.

BACKGROUND

Treatment of diseases, such as cancer, and cells using radiation therapy, radiotherapy, radiosurgery, or radiation oncology has improved over the last few decades. Doctors can treat problem areas in patients, or any living organism, using proton, heavy ion, charged ion, photon, x-ray, or gamma ray radiation therapy with relative precision and accuracy. In some cases, radiation therapy is preferred over chemotherapy or surgery as a non-invasive lower risk treatment. Even with advances in medicine, radiation treatments still present high risks to patients by potentially damaging healthy cells or not killing enough diseased cells.

Healthy cells may be damaged during radiation therapy due to uncertainty relating to beam widths, beam scattering, the true internal position of the target, real time internal movement, patient movement, patient breathing, limits of medical imaging technologies, human error, or machine targeting uncertainty. This may result in overtreating or undertreating a target area. Moreover, the treatment costs for radiation therapy can accumulate due to the number of sessions, equipment expenses, repeated medical imaging tests, or labor costs.

The use of micro-medical devices, either implantable or provided externally, is a quick growing field in medicine. With continued miniaturization and advances in nanotechnology, some medical systems now have the added advantage of having tools or machines work in vivo providing practitioners with another dimension of treatment.

It is desirable to reduce damage or exposure to healthy cells from an external radiation source while effectively treating more cells in a target area of a living organism.

SUMMARY

An apparatus and method for reducing absorption of radiation by healthy cells from an external radiation source provided to a living organism is disclosed. A smart device or apparatus with a smart antenna implanted near a target area in the living organism or provided externally proximate to the target area is provided to absorb any excess radiation. With the decrease of radiation or protection of healthy cells, higher radiation to the target area or diseased cells may be provided.

BRIEF DESCRIPTION OF THE DRAWINGS

A more detailed understanding may be had from the following description, given by way of example in conjunction with the accompanying drawings wherein.

DETAILED DESCRIPTION

Figure 1:
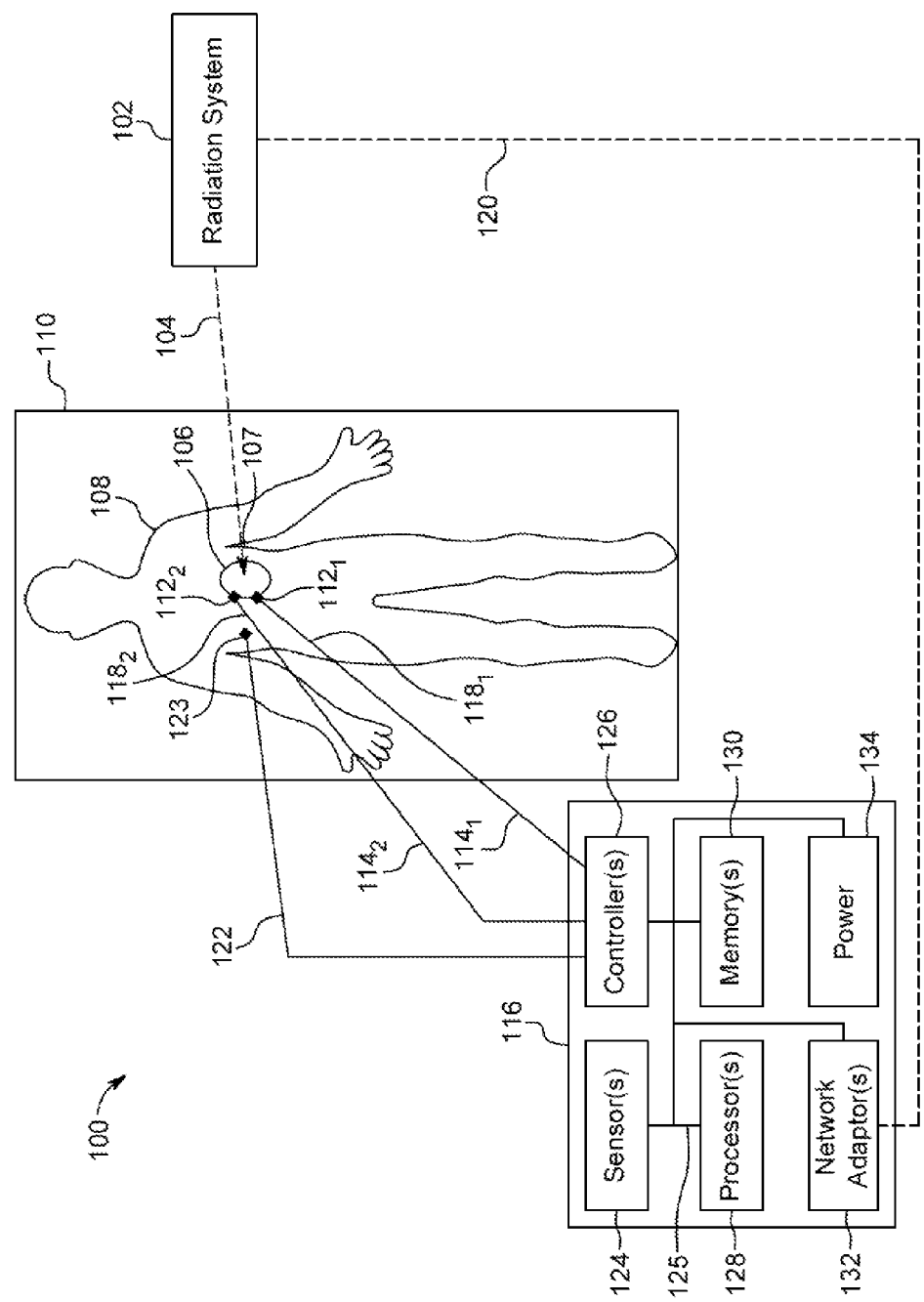
FIG. 1 is a diagram of an apparatus and system for reducing damage or exposure to healthy cells from an external radiation source.

The present embodiments will be described with reference to the drawing figures wherein like numerals represent like elements throughout. For the methods and processes described below, steps recited may be performed out of sequence in any order and sub-steps not explicitly described or shown may be performed. In addition, "coupled" or "operatively coupled" may mean that objects are linked between zero or more intermediate objects. Also, any combination of the disclosed features/elements may be used in one or more embodiments. When referring to "A or B", it may include A, B, or A and B, which may be extended similarly to longer lists. In the diagrams and figures forthcoming, in order to provide easier illustrations, the components, devices, apparatuses, or blocks shown are not drawn to scale. Different power or energy levels may be given in the embodiments below. However, the present embodiments may be configured to use any energy or power levels sufficient enough to achieve the therapeutic goals to a target area.

FIG. 1 is a diagram of an apparatus and system 100 for reducing damage or exposure to healthy cells from an external radiation source. As previously mentioned, the components in FIG. 1 are not drawn to scale. Radiation system 102 is a device that provides a radiation beam 104 to treatment or target area 106 internal or external to patient 108 on treatment table 110. Radiation system 102 may be a proton therapy, proton beam therapy, particle therapy, hadron therapy, heavy ion radiation therapy, charged ion therapy, electron therapy, photon therapy, x-ray therapy, gamma ray therapy, gamma knife therapy, cyber knife therapy, radio frequency therapy, radiosurgery, thermal ablation therapy, acoustic therapy, ultrasonic therapy, laser therapy, or radio frequency ablation therapy system. Although a single radiation beam 104 is shown, radiation system 102 may be configured to emit radiation beams from multiple sources and multiple directions to treat target area 106.

Radiation system 102 may be configured to provide treatment or operate by changing or damaging deoxyribonucleic acid (DNA) synthesis in the cells of target area 106. On a molecular level, this change or damage may be related to causing the break of chemical bonds in the cells in target area 106. The damage in the DNA structure or sequence weakens the cell and typically leads to cell death. Cell death is sometimes called apoptosis, also known as programmed cell death or self destruction. The radiation from radiation system 102 may also weaken the cells in target area 106 to a point that they will have reproductive problems or the cells will be unable to repair it's DNA. If the cells die, an area of dead tissue may form in target area 106 or white blood cells may take care of replacing the area with healthy cells. With respect to changing DNA of a cell, this may be desired for a cell that is mostly healthy but needs altering.

For a cancerous cell, triggering the cell death sequence is desired since most cancerous cells have mutations in DNA that evade apoptosis or other death sequences. Evasion is a result of cancers genes, or oncogenes, suppressing apoptosis mechanisms. In addition to apoptosis, cancer cells contain other mechanisms and characteristics, such as metastasis, that cause fast growth of a tumor, lesion, or any other mass.

With respect to proton therapy, proton beam therapy, particle radiation therapy, or radiotherapy, hydrogen protons are accelerated, typically by a cyclotron or any other particle accelerator, by radiation system 102 creating radiation beam 104. The resolution of beam 104, such as a pencil beam, may be on the order of centimeters (cms) or millimeter (mms). A benefit of proton therapy over other radiation therapies is that the maximum delivered energy or power occurs millimeters or centimeters within a patient or living organism causing little or no damage to cells, bone, or tissue at entry point 107. This maximum energy is also known as the Bragg peak. The maximum delivered energy in proton therapy may be on the order of 10s or 100s of mega electron volts (MeVs).

Another benefit of proton beam therapy is low exit beam exposure since after the Bragg peak, the energy level drops for many particles. The exit beam is in reference to radiation that goes through patient 108 after treating target area 106. Examples of proton or proton beam therapy include U.S. Pat. Nos. 5,866,912, 6,814,694, 6,873,123, 7,348,579, 7,755,068, 7,791,051, 7,801,988, and 8,067,748 and U.S. Patent Publication No. 2011/127,443 all herein incorporated by reference as if fully set forth.

Although proton therapy is relatively accurate and precise, many healthy cells around target area 106, such as the prostate, may be damaged, killed, or mutated by radiation beam 104 since human cells are only on the scale of micrometers (μms) while radiation beams may be order of magnitudes larger. Moreover, there is uncertainty to where radiation beam 104 stops with proton therapy. Using radiation reduction explained below will protect or ensure against unintentional damage to healthy tissue caused by inaccuracies of beam end points in proton and other therapies.

Heavy ions beams provided by radiation system 102 may operate similarly to proton therapies except that carbon or some other ions may be used. Unlike proton therapy, carbon ions may not have a Bragg peak drop off causing exit beam radiation exposure to healthy cells or tissue. However, other ions may be used with similar profiles of hydrogen protons by radiation system 102. An advantage of heavy ion therapy over proton therapy is the ability to provide higher dosages ensuring damage to diseased, cancer, or tumor cells. In addition to some of the references provided above for proton therapy that also describe heavy ion therapy, examples of heavy ion therapies include U.S. Pat. Nos. 6,693,283, 7,138, 771, 8,030,627, and 8,076,657 and U.S. Patent Publication Nos. 2010/187,446 all herein incorporated by reference as if fully set forth.

Unlike particle therapy photon, x-ray, or gamma ray therapies provided by radiation system 102 to target area 106 use electromagnetic radiation. The photon, x-ray, or gamma ray radiation may use two dimensional (2D) or three dimensional (3D) beam sources to treat target area 106. The beams may or may not be modulated. Power levels of these beams may be on the order of kilovolts 100's of (kVs) or 10's of megavolts (MVs). Examples of photon therapies include U.S. Pat. Nos. 7,559,945, 7,835,492, and 7,902,530 and U.S. Patent Publication Nos. 2009/063,110, 2010/074,400, 2010/ 272,241, 2011/085,640, and 2011/240,874. Unlike particle or proton therapies, photon beams provided by radiation system 102 may damage healthy cells, tissue, or bones on entry and exit of radiation beam 104.

Moreover, radio frequency, thermal ablation, acoustic, ultrasonic, laser, or radio frequency ablation therapies provided by radiation system 102 may use electromagnetic radiation, such as microwave, to heat up target area 106. Unlike previously explained therapies, radiation system 102 may be configured to provide exposure to target area 106 in vivo using a probe (not shown) for radio frequency, thermal ablation, acoustic, ultrasonic, laser, or radio frequency ablation therapies. Examples of these therapies include U.S. Pat. Nos. 6,322,560, 6,936,046, 7,419,500, 7,792,566 and U.S. Patent Publication Nos. 2006/280,689, 2008/082,026, 2009/ 294,300, 2009/306,654, 2010/125,225, 2010/179,522, 2010/ 298,821, 2011/125,143, 2011/166,437, and 2011/306,881. Unlike particle or proton therapies, these treatments provided by radiation system 102 may damage healthy cells, tissue, or bones on entry and exit of radiation beam 104.

Target area 106 may include diseased cells, viral cells, infected cells, cancer cells, healthy cells, normal cells, abnormal cells, infected tissue, normal tissue, abnormal tissue, deep tissue, a benign tumor, a malignant tumor, a cancerous tumor, neoplasm, cyst, or a lesion. Target area 106 may be internal, partially internal, external, or partially external to patient 108. Although shown in the chest area of patient 108, target area 106 may be located anywhere in patient 108 such as the head, brain, spine, neck, any organ, bones, limbs, breasts, reproductive areas, hands, feet, etc. Target area 106 may also be of any size. For instance, a tumor may be 1 cm-10 cm.

Flexible or semi-flexible probe, electrode, rod, or catheter devices $114_1$ and $114_2$ having devices $112_1$ and $112_2$ may be implanted directly into patient 108 through points $118_1$ and $118_2$, respectively. Devices $114_1$ and $114_2$ may also be rigid or semi-rigid. Alternatively, devices $114_1$ and $114_2$ may be thin surgical needles or biopsy needles used to implant or inject devices $112_1$ and $112_2$. Devices $112_1$ and $112_2$ may be implanted temporarily during a pre-radiation outpatient procedure or during the first radiation treatment. Devices $112_1$ and $112_2$ may be left in the body for the days or weeks needed for the radiation treatment.

Before each subsequent treatment, devices $114_1$ and $114_2$ may be repositioned in order to ensure proper radiation absorption around target area 106 by devices $112_1$ and $112_2$. Moreover, local anesthesia may be used at points $118_1$ and $118_2$ of patient 108 during implantation. Implantation may be assisted by ultrasound, functional magnetic resonance imaging (FMRI), computed tomography (CT) scan, computed axial tomography (CAT) scan, positron emission tomography (PET) scan, or any other medical imaging technologies to ensure proper placement near target area 106. Devices $112_1$ and $112_2$ are eventually removed using a similar medical procedure used for implantation.

General anesthesia or sedation of patient 108 may be used during implantation. Points $118_1$ or $118_2$ may be veins or arteries used to access target area 106 in order to not cause damage to organs or tissues while implanting device $112_1$ and $112_2$. In addition, devices $112_1$ and $112_2$ may be implanted via the nose, mouth, or anus cavity of patient 108. Devices $112_1$ and $112_2$ may be placed proximate, adjacent, next to, or within target area 106. With some tumors or diseased cell areas care should be taken when positioning devices $112_1$ and $112_2$ to not disturb and spread the cells to other areas around target area 106. Moreover, devices 112$_1$ and 112$_2$ may be provided in any shape suitable for implantation.

In the case of ion particle radiation, device 112$_1$ is configured to reduce, mitigate, or absorb radiation power of healthy cells around, near, at a close distance, proximate, adjacent, or within target area 106 from radiation system 102 by using smart antennas, an adaptive antenna, an adaptive antenna array, a phased antenna array, sectored antennas, a switched antenna array, a switched phased conducting array, beamforming, beamsteering, beam shaping, or multiple antennas. A smart antenna array on device 112$_1$ dynamically generates or produces receive beams to capture, disperse, nullify, harvest, or collect excess scattered particles, scattered molecules, excess ions, excess charge, excess energy, partial excess energy, near-field energy, rogue particles, free radicals, stray particles, misguided particles, off target particles, electromagnetic radiation, or residual radiation caused by radiation beam 104. The smart antenna array may include capacitive, inductive, magnetic device elements or fields for capturing excess protons or electromagnetic radiation power, as will be explained further below. The capturing may be done in part or substantially to reduce radiation levels enough to where chemical bonds are kept in tact in cells around target area 106 keeping them unharmed.

Figure 3A:
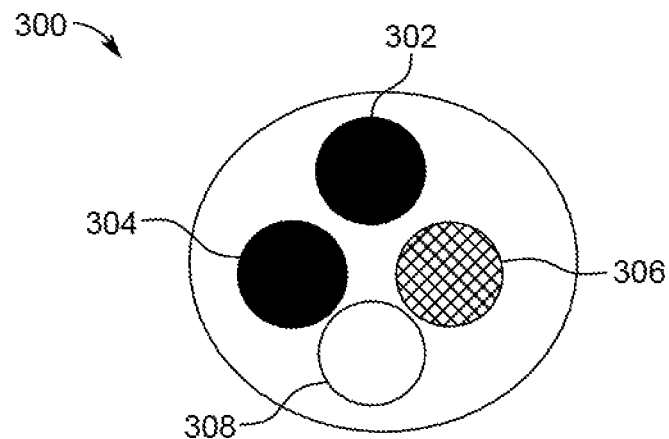
FIGS. 3a-3d are diagrams of probes, electrodes, rods, catheters, or implantation devices for reducing damage or exposure to healthy cells from an external radiation source.
Figure 3B:
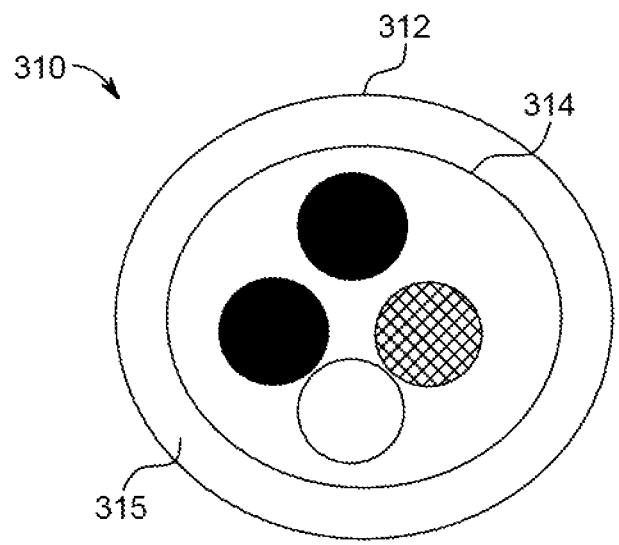
Figure 3C:
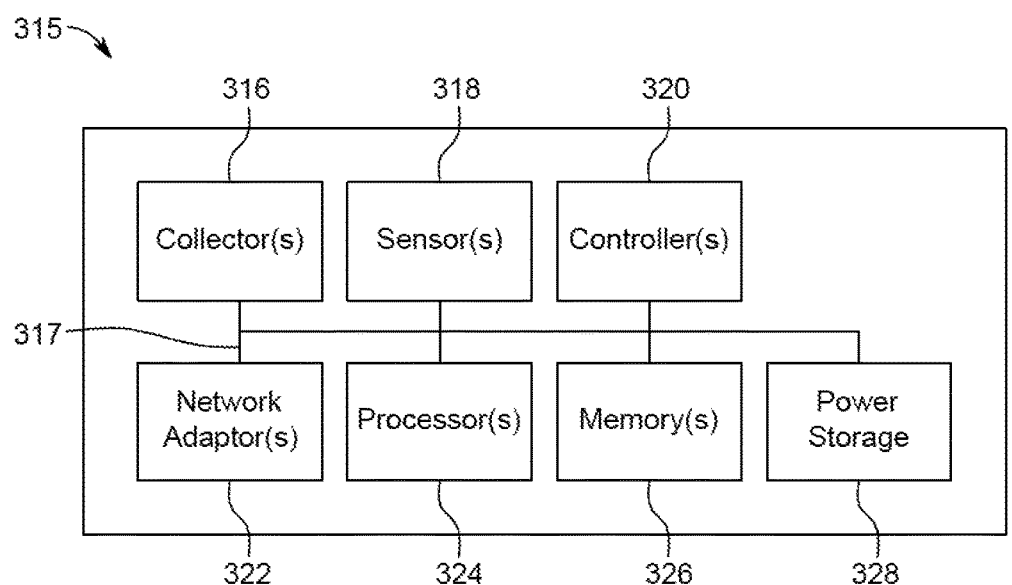
Figure 3D:
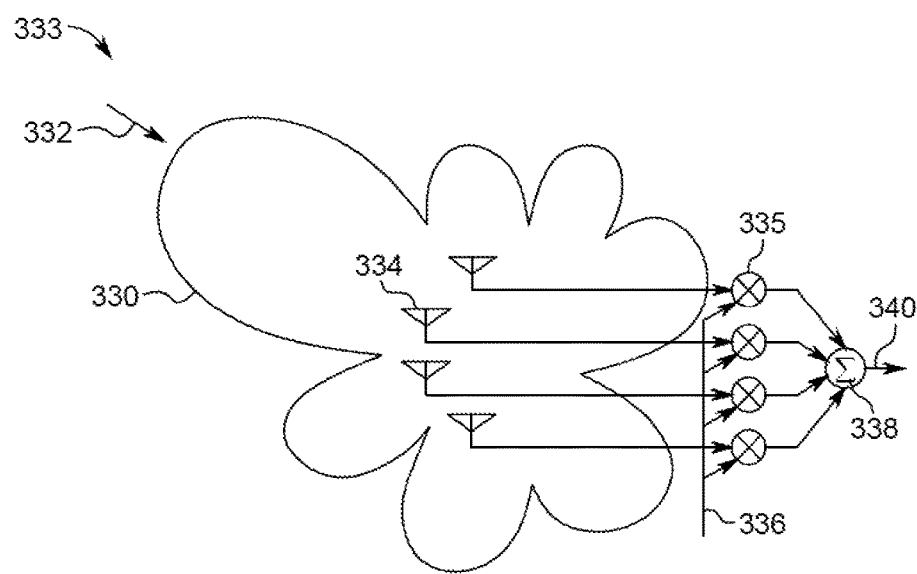

FIG. 3d is an implantable smart antenna array 333 that may be used on device 112$_1$. Excess particles or radiation energy may be captured or received by adaptive receive beam 330 generated by antennas 334. Although receive beam 330 is shown from a two dimensional (2D) side view in FIG. 3d, the lobe expands and exists in three dimensions (3D). Adaptive receive beam 330 may be generated by controlling or varying amplitude and phase weights 335 such that energy or particles 332 in the direction of beam 330 are mostly captured while energy or particles outside of the area of receive beam 330 are minimally disturbed. Weights 335 may also be configured as a mixer used to tune into different frequencies in order to capture maximum scattered energies. Weights 335 may be software programmable or hardware configurable by control signal 336. The received energy by antennas 334 is summed by summer 338 based the different values of phase and weights 335 and outputted as current or signal 340.

The captured radiation energy or power of smart antenna array 333 is roughly given by equation 1:

$$P_{captured} = S * A_e (\text{WATTS})$$

where S is the power density (W/m$^2$) of energy or particles 332 and A$_e$ (m$^2$) is the antenna effective aperture. The ability to capture energy by smart antenna array 333 is greatest when the effective aperture value is large. This is the case when using low resistance and highly conductive materials. Directionality of adaptive receive beam 330 increases receive gain and a higher aperture value resulting in a higher P$_{captured}$.

Smart antenna array 333 may be implemented as multiple pronged elements, a spherical antenna, a curved antenna, a crescent shaped antenna, a satellite shaped antenna, a directional antenna, programmable fractal elements, a patch antenna array, or a nanoantenna array. Moreover, smart antenna array 333 may be a printed antenna array of medically safe implantable metals, electromagnets, nanomagnets, minimagnets, nanoreceptors, or nanoparticles. An example of a safe implantable metal may be gold. Examples of nanomagnets are given in U.S. Pat. No. 6,828,786 herein incorporated by reference as if fully set forth. Smart antenna array 333 may produce beams of different sizes and shapes depending on the radiation therapy system and treatment.

Referring again to FIG. 1, devices 112$_1$ and 112$_2$ are controlled by one or more controller device 126 in radiation reduction device 116. Coupled to one or controller device 126 via bus or interconnectors 125 are one or more sensors 124, one or more processors 128, one or more memory devices 130, one or more network adapters 132, and power source 134. Radiation reduction device 116 may have other components or subcomponents not shown in FIG. 1 or may be configured without one or more of the components shown in FIG. 1.

One or more network adapters 132 may be configured as an Ethernet, 802.x, fiber optic, Frequency Division Multiple Access (FDMA), single carrier FDMA (SC-FDMA), Time Division Multiple Access (TDMA), Code Division Multiple Access (CDMA), Orthogonal Frequency-Division Multiplexing (OFDM), Orthogonal Frequency-Division Multiple Access (OFDMA), Global System for Mobile (GSM) communications, Interim Standard 95 (IS-95), IS-856, Enhanced Data rates for GSM Evolution (EDGE), General Packet Radio Service (GPRS), Universal Mobile Telecommunications System (UMTS), cdma2000, wideband CDMA (W-CDMA), High-Speed Downlink Packet Access (HSDPA), High-Speed Uplink Packet Access (HSUPA), High-Speed Packet Access (HSPA), Evolved HSPA (HSPA+), Long Term Evolution (LTE), LTE Advanced (LTE-A), 802.11x, Wi-Fi, Zigbee, Ultra-WideBand (UWB), 802.16x, 802.15, Wi-Max, mobile Wi-Max, Bluetooth, radio frequency identification (RFID), Infrared Data Association (IrDA), near-field communications (NFC), or any other wireless or wired transceiver for modulating and demodulating signals.

One or more sensors 124 may be motion, proximity, light, optical, chemical, environmental, moisture, acoustic, heat, temperature, radio frequency identification (RFID), biometric, image, photo, or voice recognition sensors. One or more sensors 124 may also be an accelerometer, an electronic compass (e-compass), gyroscope, a 3D gyroscope, or the like. Moreover, one or more controllers 126 may include a display controller for controlling a display device, a touch screen display device, a multi-touch display device, or a three dimensional (3D) display device.

One or more network adapters 132 may communicate via wired or wireless link 120 with radiation system 102 to provide feedback, beamforming information, calibration, targeting assistance, or coordination in conjunction with device 112$_1$. For instance, smart beams produced by device 112$_1$ may be timed to be synchronized with the expected maximum proton energy time at target area 106. This may insure that any fields generated by device 112$_1$ do not distract or interfere with the path of radiation beam 104. Radiation system 102 may also provide feedback on the beamforming pattern of device 112$_1$. This may be based on real-time medical imaging feedback obtained by radiation system 102. In addition, link 120 may be used to configure or calibrate radiation system 102 or assist radiation system 120 with adjusting radiation given to target area 106.

In the case of photon radiation provided by radiation system 102, device 112$_2$ may be configured with one or more miniature photo diodes, photo detectors, or photo sinks. This configuration will be explained in more detail below. Alternatively, device 112$_2$ may be configured similar to device 112$_1$ for providing radiation absorption from another angle or position relative to target area 106. Providing coverage from multiple points around target area 106 may be increased by using a plurality of devices 112$_1$ and 112$_2$.

In addition, devices $112_1$ and $112_2$ may be configured to be implanted with devices $114_1$ and $114_2$ being detached after implantation as shown in FIG. 3c. Device 315 comprises one or more controller devices 320 coupled to, via bus or interconnectors 317, one or more sensors 318, one or more processors 324, one or more memory devices 326, one or more network adapters 322, and power storage 328. Device 315 may have other components or subcomponents not shown in FIG. 3c or may be configured without one or more of the components shown in FIG. 3c. One or more network adapters 322 or one or more sensors 318 may be configured as described above for radiation reduction device 116. Device 315 may be configured to activate or energize, similar to a radio frequency identification (RFID) tag, by using the electromagnetic near-field energy around target area 106 using one or more collector devices 316. One or more collector devices 316 may act as an energy source for device 315 and be configured with smart antennas to generate receive beams to collect excess energy from radiation system 102 as previously explained. The smart antenna beamforming information may be preprogrammed on device 315 or dynamically programmed using an RFID programmer or writer. Moreover, tissue safe barbs or fasteners may be used to keep device 315 proximate to target area 106.

Referring again to FIG. 1, for some treatments flexible or semi-flexible probe, or electrode device 122 with radiation reduction device 123 may be used. Radiation reduction device 123 may be a patch that attaches externally to patient 108 that is configured similar to devices $112_1$ and $112_2$ explained above with smart antennas or conductors. Device 123 may be useful when target area 106 is near the epidermal or dermis layers of patient 108. Since placed externally, although device 123 may not prevent exit beam radiation exposure, it is less invasive than implanting devices $112_1$ and $112_2$.

Figure 2A:
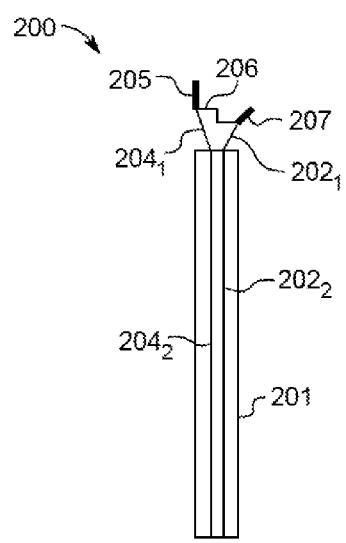
FIGS. 2a-2c are diagrams of probe, electrode, rod, or catheter implantation devices for reducing damage or exposure to healthy cells from an external radiation source.
Figure 2B:
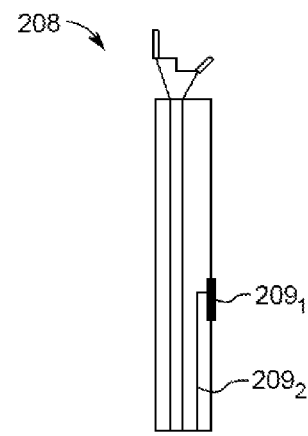
Figure 2C:
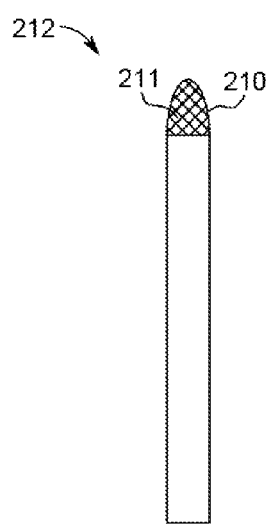
Figure 2D:
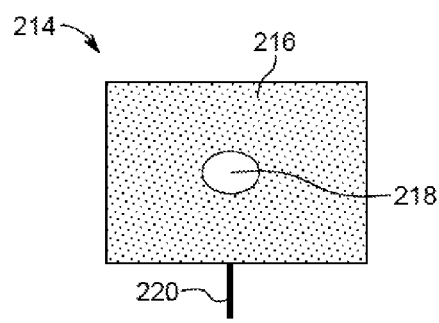
FIG. 2d is a diagram of an external device used for reducing damage or exposure to healthy cells from an external radiation source.

FIG. 2d is a diagram of an external device 214 used for reducing damage or exposure to healthy cells from an external radiation source. External device 214 may be attached to patient 108's skin. Adaptive fields, electric or magnetic, emitted by phased array devices 216 are used to guide or absorb ions, such as protons, from radiation beam 104 for target area 106 through hole or pin hole 218. Control of external device 214 may be provided by wire, line, or cable 220. External device 214 helps to ensure that radiation beam 104 does not miss target area 106 by guiding ions through hole or pin hole 218 by emitting an adaptive field by phased array devices 216. If an ion is off target, such as due to patient 108 movement or target modeling errors, it is absorbed by phased array devices 216 as explained below and prevented from damaging any healthy tissue by the entry or exit of radiation beam 104.

FIGS. 2a-2c are diagrams of probes, electrodes, rods, and catheter implantation devices for reducing damage or exposure to healthy cells from an external radiation source. In FIG. 2a, device 200 may be flexible, semi-flexible, semi-rigid, or rigid and includes protective sheath or outer layer 201. Device 206 may include of one or more antenna or exposed conductor elements that have controllable receive beams. Exposed conductor elements may be coated or sealed with a conducting polymer or material to protect metal, such as gold, silver, or copper, used to make the conductor elements in device 206 against contaminating target area 106 or tissue around target area 106. One or more lead lines, cables, or wires $204_1$ and $204_2$ are coupled to one end of device 206 to provide control signals to device 206 from one or controller device 126. One or more lead lines, cables, or wires $202_1$ and $202_2$ are coupled to the other end of device 206 for providing a drain or sink for the excess radiation power captured device 206 to one or controller device 126. Alternatively, the functionality and purpose of one or more lead lines, cables, or wires $204_1$ and $204_2$ may be switched with one or more lead lines, cables, or wires $202_1$ and $202_2$.

In one embodiment, device 206 may provide a current or voltage for attracting excess scattered particles, scattered molecules, excess ions, excess charge, excess energy, partial excess energy, near field energy, rogue particles, stray particles, misguided particles, off target particles, or residual radiation caused by radiation beam 104 to tissue around target area 106. Attraction may be caused by controllable net negative or net positive currents or voltages provided by one or more lead lines, cables, or wires $204_1$ and $204_2$ to generate controllable magnetic or electric fields. When ionizing radiation beam 104 is positive, a net negative current or voltage source may be used to provide a force to attract stray or excess proton radiation. The power level of the net negative current or voltage may depend on the positive charge level of the protons.

Conversely, when the ionizing radiation beam 104 is negative, a net positive current or voltage source may be used to provide a force to attract stray or excess electron radiation. The power level of the net positive current or voltage may depend on the negative charge level of the electrons. The net positive or negative currents may be provided on a modulated or sinusoidal signal to device 206 by one or more lead lines, cables, or wires $204_1$ and $204_2$. The frequency of the modulated or sinusoidal signals may be related to that of radiation beam 104. In addition, the net positive or negative currents may be direct or alternating currents and modulated such that it provides adaptive magnetic fields to capture excess radiation. The antenna array may be an array of coils that are phase controlled to provide adaptive magnetic fields. For using electric fields, device 206 may be configured as an array of minicapacitors or nanocapacitors that provide Coulomb forces to capture or slow down stray particles from radiation beam 104.

Moreover, net magnetic fields or electromagnetic fields provided and made directional using smart antenna receive beamforming by device 206 may be used for energy transfer from stray particles. These fields may be adjustable or adaptive by providing control signals to device 206 via one or more lead lines, cables, or wires $204_1$ and $204_2$ to provide different Lorentz forces. Moreover, an array of magnets, nanomagnets, or electromagnets in device 206 in combination with a smart antenna array may be used to generate an adaptive magnetic field pattern for capturing stray ions. Antenna elements or portions 205 and 207 may be used with device 206 to adjust electric or magnetic fields. In the examples above, when an attracted ion, such as a proton, hits conductor elements in device 206 current, heat, or light is generated due to the energy transfer and/or chemical bonding of the ions to the conductor elements. For instance, a hydrogen proton may bond to an electron in the conductor elements of device 206.

In addition to absorption, magnetic or electric fields adaptively provided by device 206 may slow down, catch, or deflect a stray ion or proton by absorbing some of its energy without removing the particle. By slowing down the particle, enough energy may be absorbed where the ion no longer can cause damage to cells around target area 106. For instance, if a proton with energy in radiation beam 104 is slowed from 200 MeV to 10 MeV damage to healthy cells may be prevented. The particle or proton may then harmlessly bond with a cell in patient 108.

With respect to deflection, device 206 may use magnetic fields similar to those used in radiation system 102 for deflecting stray ions or protons back to target area 106 and away from health tissue around target area 106. This may be done such that the energy level of the ions or protons is maintained thereby still treating diseased cells within target 106.

For device $112_2$, device 206 may be configured with photo diodes, photo detectors, or photo sinks to capture any excess or stray photons from damaging any healthy tissue around target area 106 or causing exit beam damage. When an x-ray or gamma ray hits the photo diodes, photo detectors, or photo sinks, a current is generated during the energy transfer. With device 206 having smart antenna systems, the photo diodes are provided directionality and focus such that they do not interrupt photons that are needed to treat target area 206.

In addition, devices $112_1$ and $112_2$ may be combined so that any stray photons caused by proton scattering are captured before exposure to healthy cells. The beam generated by devices $112_1$ and $112_2$ may be coordinated by one or more controller device 126 for this and other configurations.

In FIG. 2b, device $209_1$ may be used with probe, electrode, rod, or catheter implantation device 208 for absorbing any excess radiation on entry of radiation beam 104 by using smart antenna receive beamforming. The adaptive receive beams for device $209_1$ may be provided by one or more lead lines or wires $209_2$. Device 208 may be placed at selective gaps or openings along the radiation beam 104 path depending on the configuration of radiation system 102 and position of target area 106. Via link 120, the adaptive beam pattern provide by device $209_1$ may be timed such that it is activated slightly after particles in radiation beam 104 have passed on the way to target area 106. This may prevent any disruption to radiation beam 104 while providing the benefits of absorbing any excess radiation, as explained in part above.

FIG. 2c shows a different configuration where device 206 is implanted by probe, electrode, rod, or catheter implantation device 212. Tip or point 210 encapsulates device 206 with smart antenna array 211 in an elongated, capsule like structure.

FIGS. 3a and 3b show interior views of probe, electrode, rod, or catheter implantation devices. In FIG. 3a, device 300 comprises of lead lines or wires 302 or 304, signaling line 306, and fiber optic camera device 308. Fiber optic camera device 308 may be used to assist the physician or surgeon during implantation and repositioning of devices 206, 208, or 210.

In FIG. 3b, a layer of electroactive polymer (EAP) material 315 may be placed between safety layer or lining 312 and interior layer or lining 314 of probe, electrode, rod, or catheter implantation device 310. EAPs are polymers that exhibit a change in size or shape when stimulated by an electric field. The size and shape can be controlled such that device 310 can moves within patient 108. One or more controllers 126 may control the initial placement and possible subsequent movement of devices $112_1$ and $112_2$.

Figure 4:
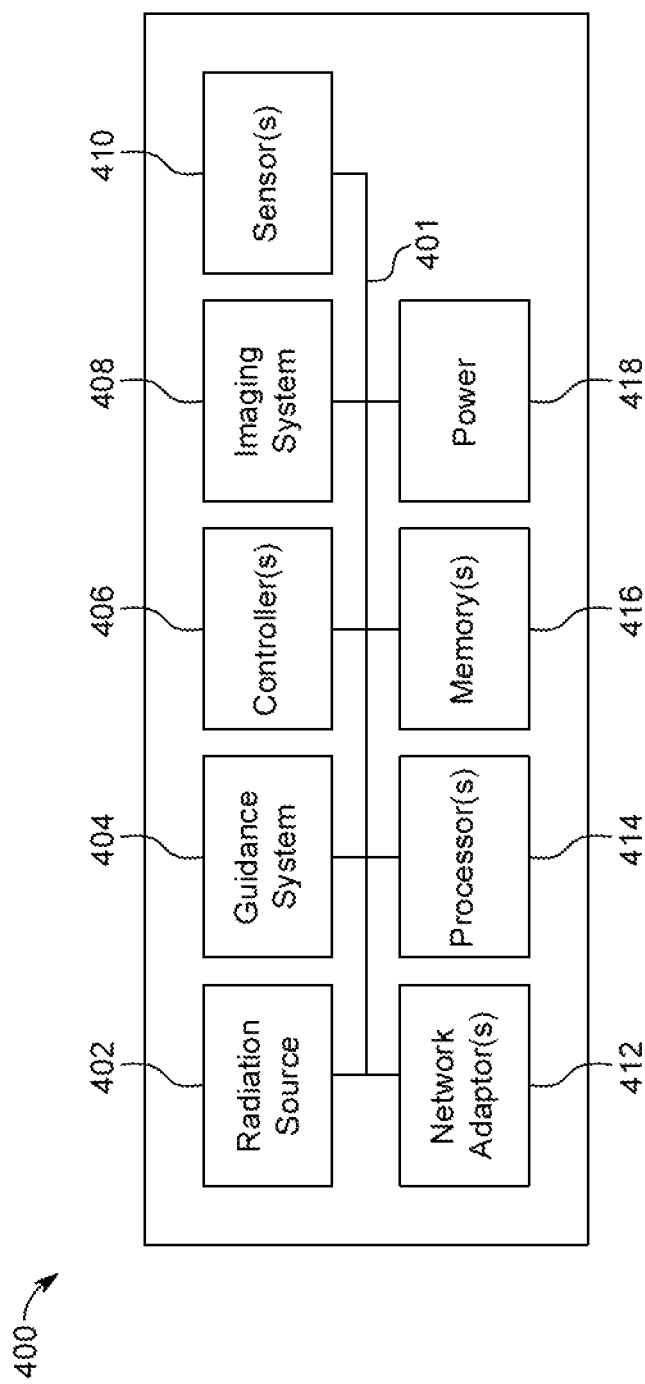
FIG. 4 is a diagram of a radiation system device.

FIG. 4 is a diagram of radiation system device 400 that may be used for the examples provided above. Radiation source 402 is coupled via bus or network 401 to beam guidance system 404, one or more controller devices 406, imaging system 408, one or more sensors 410, one or more network adapters 412, one or more processors 414, one or more memory devices 416, and power source 418. Device 400 may have other components or subcomponents not shown in FIG. 4 or may be configured without one or more of the components shown in FIG. 4. One or more network adapters 412 or one or more sensors 410 may be configured as described above for radiation reduction device 116.

Figure 5:
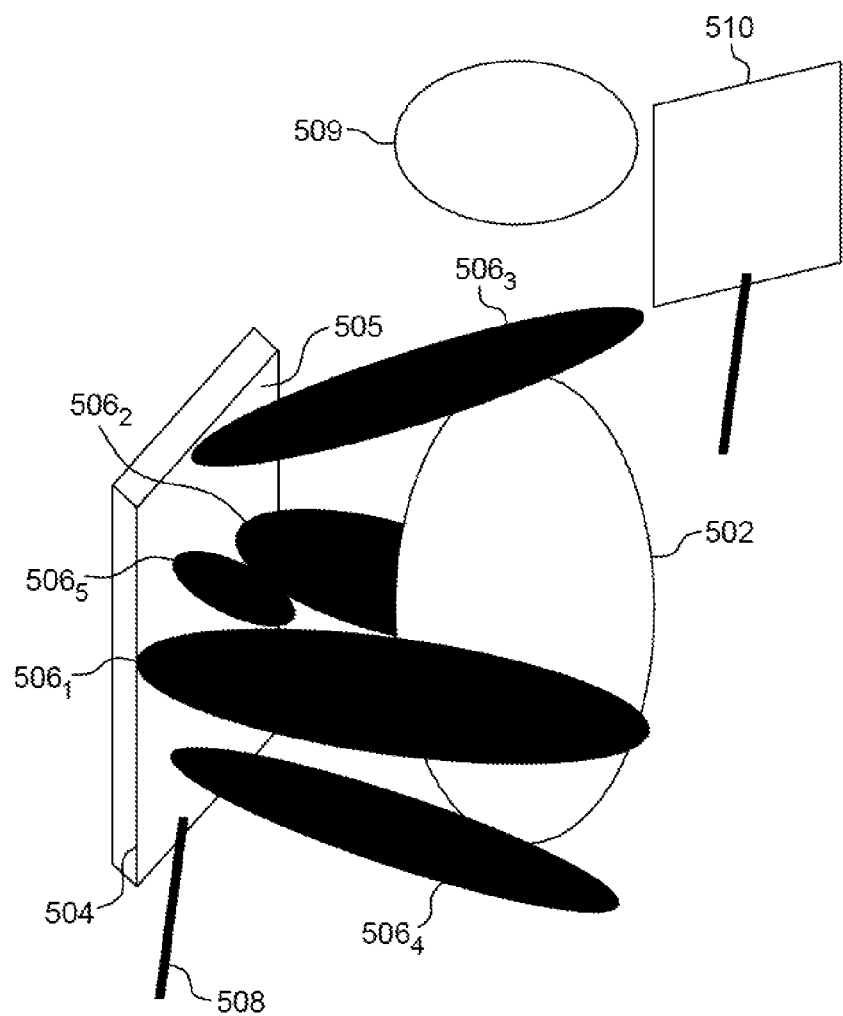
FIG. 5 is a diagram of a smart antenna device for reducing damage or exposure to healthy cells from an external radiation source.

FIG. 5 is a diagram of a device 504 for reducing damage or exposure to healthy cells from an external radiation source. As previously noted, the components shown in FIG. 5 are not drawn to scale. Device 504 is placed near target area 502. In the example shown in FIG. 5, smart antenna array 505 generates adaptive receive beams $506_1$-$506_5$ via control signals sent over line or wire 508 by one or more controllers 126. The adaptive receive beams shown in FIG. 5 may be generated by adaptive voltage sources, current sources, magnetic fields, or electric fields as explained above. Beams $506_1$ and $506_2$ may protect healthy cells lateral to target area 502 by absorbing excess radiation power from radiation beam 104, as explained above. Similarly, beams $506_3$ and $506_4$ may protect healthy cells on the top or bottom of target area 502. Beam $506_5$ may protect healthy cells located behind target area 502. An example of a protected area is area 509.

In order to protect healthy cells from other angles, a second device 510, configured similar to device 504, may be placed near target area 502. The beam generated by devices 504 and 510 are coordinated by one or more controllers 126. Although device 504 is drawn to be substantially planar, it may be in any shape suitable for implantation. Example shapes include, spherical, cylindrical, capsule shaped, cubical, an elongated sphere, etc.

Figure 6:
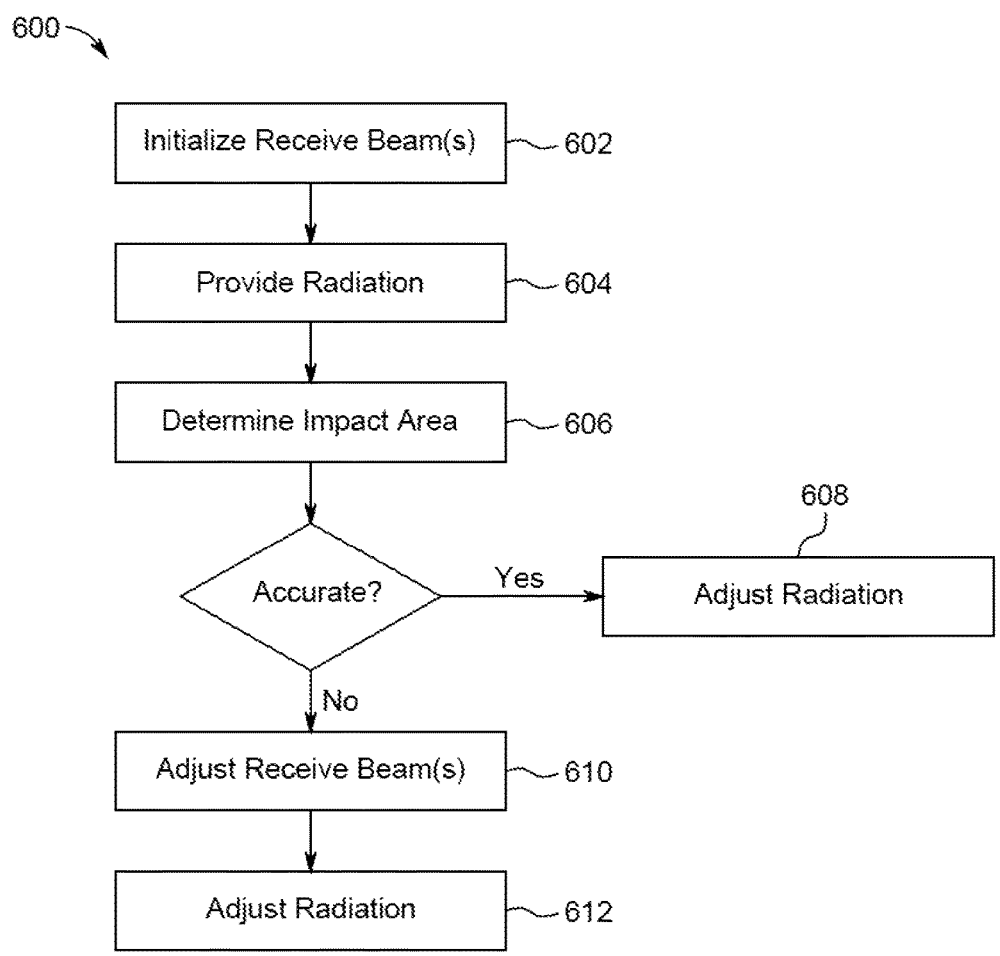
FIG. 6. is a process for reducing damage or exposure to healthy cells from an external radiation source.

FIG. 6 is a process 600 for reducing damage or exposure to healthy cells from an external radiation source. Adaptive receive beams on an implanted device having a smart antenna array are initialized in part depending on the 3D modeling of a target area (602). The adaptive receive beams may be generated by adaptive voltage sources, current sources, magnetic fields, or electric fields as explained above. A radiation system provides a radiation beam to the target area (604). The impact area of the radiation beam is determined in part based on medical imaging or information collected by the implanted device (606). An external medical imaging system may also assist in determining the impact area of the radiation beam. If the radiation beam was off target, the receive beams are adjusted (610) on the smart antenna array. Subsequently, the radiation beam of the radiation is adjusted (612). If the radiation beam was accurate, the radiation system may increase or decrease the power level of the current or next radiation beam (608).

In the examples provided above, since tissue around target area 106 may be protected, such as from overshooting target area 106, higher power ions or photons may be used by radiation beam 104. The higher power or dosages may help to treat target area 106 quicker and more efficiently. This may result in lower costs due to less treatment time length per patient and less number of repeat visits per patient while increasing treatment success rates. In addition, for very sensitive areas like the brain or eyes, less damage is caused to organs surrounding target area 106. As an example, treatment of the brain may result in less memory loss for patient 108. Also, areas that may otherwise not be treatable due to vital organs surrounding target area 106, such as the pancreas, may now be treatable using the embodiments given above.

Moreover, reduction of radiation exposure due to patient movement is desirable since patient movement can move target area 106 0.5 cm-2 cm, causing offshoots when proton beam sizes are on the order of millimeters. This is especially important for pediatric oncology where a young patient needs to be sedated in order to stay still. With the embodiments above, sedation of young patients may not be necessary. In addition, certain pediatric tumors that were untreatable due to the possible threat of radiation exposure to still developing or growing organs may be feasible with the embodiments given above.

With respect to cosmetic or therapeutic treatments, the radiation reduction system provided above may be used to treat surface cells, epidermal cells, or modify nerves in patient 108. This may be useful for neurosurgical, orthopedic, or other similar procedures.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), flash memory, a register, cache memory, semiconductor memory devices, magnetic media such as internal hard disks and removable disks, magneto-optical media, and optical media such as CD-ROM disks, and digital versatile disks (DVDs).

What is claimed is:

1. A method performed by a semi-flexible rod, the method comprising:
   providing, by a substantially round tip having metal conductor elements in a fractal pattern, an adaptive electrical field or an adaptive magnetic field;
   adjusting, based on a control signal by a controller electrically coupled to the elements, energy of the adaptive electrical field or the adaptive magnetic field; and
   attracting, based on the adjustment of the energy, a stray x-ray photon near an in-vivo target area of cancer cells.

* * * * *